United States Patent
Ustuner et al.

(10) Patent No.: US 9,414,805 B2
(45) Date of Patent: Aug. 16, 2016

(54) SPECTRAL DOPPLER WITH MULTIPLE SPATIALLY DISTINCT GATES

(75) Inventors: Kutay F. Ustuner, Mountain View, CA (US); Paul D. Freiburger, Seattle, WA (US); Seshadri Srinivasan, Mountain View, CA (US); Steve Henderson, Menlo Park, CA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1557 days.

(21) Appl. No.: 12/180,775

(22) Filed: Jul. 28, 2008

(65) Prior Publication Data
US 2010/0022884 A1     Jan. 28, 2010

(51) Int. Cl.
| | | |
|---|---|---|
| A61B 8/06 | (2006.01) | |
| A61B 8/00 | (2006.01) | |
| G01S 7/52 | (2006.01) | |
| A61B 8/08 | (2006.01) | |
| A61B 8/13 | (2006.01) | |
| G01S 15/89 | (2006.01) | |

(52) U.S. Cl.
CPC . *A61B 8/06* (2013.01); *A61B 8/461* (2013.01); *G01S 7/52066* (2013.01); *G01S 7/52071* (2013.01); *G01S 7/52095* (2013.01); *A61B 8/08* (2013.01); *A61B 8/13* (2013.01); *A61B 8/488* (2013.01); *G01S 15/8979* (2013.01)

(58) Field of Classification Search
CPC .............. A61B 8/06; A61B 8/08; A61B 8/13; A61B 8/461; A61B 8/488; G01S 15/8979; G01S 7/52066; G01S 7/52071; G01S 7/52095
See application file for complete search history.

(56) References Cited

U.S. PATENT DOCUMENTS

| | | | | |
|---|---|---|---|---|
| 5,287,753 A | * | 2/1994 | Routh et al. | 600/454 |
| 5,291,892 A | | 3/1994 | O'Donnell | |
| 5,365,929 A | * | 11/1994 | Peterson | 600/455 |
| 5,409,010 A | * | 4/1995 | Beach et al. | 600/455 |
| 5,429,137 A | * | 7/1995 | Phelps et al. | 600/455 |
| 5,485,844 A | * | 1/1996 | Uchibori | 600/455 |
| 5,634,465 A | * | 6/1997 | Schmiesing et al. | 600/454 |
| 5,675,554 A | | 10/1997 | Cole et al. | |
| 5,868,676 A | * | 2/1999 | McCabe et al. | 600/454 |
| 6,030,345 A | * | 2/2000 | Wang | 600/454 |
| 6,110,118 A | * | 8/2000 | Guracar et al. | 600/453 |

(Continued)

FOREIGN PATENT DOCUMENTS

WO    WO2004/082461    3/2004

OTHER PUBLICATIONS

Bascom et al., 1995 ("Defining the limitations of measurements from Doppler spectral recordings").*

(Continued)

*Primary Examiner* — Katherine Fernandez (57) ABSTRACT

Spatially distinct Spectral Doppler information is displayed. A spectrum is determined for each of a plurality of spatial locations, such as associated with different receive beams. Given a plurality of spectra at different spatial locations, an image may be generated as a function of the spectra. For example, a two-dimensional image has display values for different pixels or locations derived from one or more characteristics of the spectra, such as the maximum velocity with energy above a threshold for each location. As another example, the spectrum from the set of spectra with the highest maximum velocity is selected for generating a spectral strip display.

19 Claims, 2 Drawing Sheets

(56) References Cited

U.S. PATENT DOCUMENTS

| | | | |
|---|---|---|---|
| 6,374,128 B1 * | 4/2002 | Toida et al. | 600/310 |
| 6,390,980 B1 | 5/2002 | Peterson et al. | |
| 6,616,611 B1 * | 9/2003 | Moehring | 600/454 |
| 6,663,566 B2 * | 12/2003 | Pan et al. | 600/454 |
| 2003/0013962 A1 * | 1/2003 | Bjaerum et al. | 600/443 |
| 2005/0033175 A1 * | 2/2005 | Lee et al. | 600/453 |
| 2005/0043622 A1 | 2/2005 | Jensen | |
| 2005/0137479 A1 * | 6/2005 | Haider | 600/440 |
| 2006/0052698 A1 * | 3/2006 | Loupas | 600/437 |
| 2007/0161898 A1 * | 7/2007 | Hao et al. | 600/443 |
| 2008/0059098 A1 * | 3/2008 | Zhang | 702/103 |
| 2010/0234731 A1 * | 9/2010 | Lu et al. | 600/454 |

OTHER PUBLICATIONS

Steinman et al., "Sources of Error in Maximum Velocity Estimation using Linear Phased-Array Doppler Systems with Steady Flow", Ultrasound in Med. & Biol., vol. 27, No. 5, pp. 655-664, 2001.*

B. Dunmire, et al., "Cross-Beam Vector Doppler Ultrasound for Angle-Independent Velocity Measurements", Ultrasound in Med. & Biol., vol. 26, No. 8, pp. 1213-1235, 2000.

P.R. Hoskins, "A Comparison of Single- and Dual-Beam Methods for Maximum Velocity Estimation", Ultrasound in Med. & Biol., vol. 25, No. 4, pp. 583-592, 1999.

* cited by examiner

SPECTRAL DOPPLER WITH MULTIPLE SPATIALLY DISTINCT GATES

BACKGROUND

The present invention relates to Spectral Doppler ultrasound. Spectral Doppler ultrasound imaging provides an image of velocities (vertical axis) values modulated by energy as a function of time (horizontal axis). This spectrum may be used for studying fluid flow within a patient. By transmitting a plurality of pulses at a single gate location, a Spectral Doppler response is generated in response to received echo signals. The frequency spectrum of the object's motion or flow for a single spatial region is estimated and displayed as a function of time.

Sonographers manually adjust the gate location, gate size, transmit frequency and other Spectral Doppler imaging control parameters in order to acquire a desirable image. Some processes have been proposed for automatic placement of the Spectral Doppler gate. The Spectral Doppler ultrasound imaging provides frequency information for a location, so may not provide spatial information. Spectral information may be provided for different depths along a same scan line. Spectral information for other locations or scan lines is acquired sequentially.

Spatial flow may be represented by Color Doppler imaging. The mean Doppler frequency shift or mean velocity for each of a plurality of spatial locations along multiple scan lines is acquired. The mean velocities are mapped to colors. However, mean velocity, such as derived from the change in frequency for Doppler processing, may not provide sufficient information regarding motion.

BRIEF SUMMARY

By way of introduction, the preferred embodiments described below include methods, systems, computer readable media, and instructions for displaying spatially distinct Spectral Doppler information. A spectrum is determined for each of a plurality of spatial locations, such as associated with different receive beams and/or depths. Given a plurality of spectra at different spatial locations, an image may be generated as a function of the spectra. For example, a two-dimensional image has display values for different pixels or locations derived from one or more characteristics of the spectra, such as the maximum velocity with energy above a threshold. As another example, the spectrum with the highest maximum velocity is selected from the set of spectra for generating a spectral strip display.

In a first aspect, a method is provided for displaying spatially distinct Spectral Doppler information. Spatial and temporal ultrasound samples are obtained for a plurality of spatially distinct locations. A spectrum is estimated for each of the spatially distinct locations from the temporal ultrasound samples. An image is displayed. The image is a function of the spectra for the plurality of spatially distinct locations.

In a second aspect, a computer readable storage medium has stored therein data representing instructions executable by a programmed processor for displaying spatially distinct Spectral Doppler information. The storage medium includes instructions for calculating a first spectrum for a first spatial location and a first period, calculating a second spectrum for a second spatial location and the first period, the second spatial location different than the first spatial location, and generating an image as a function of the first and second spectra.

In a third aspect, a system is provided for displaying spatially distinct Spectral Doppler information. A transmit beamformer is operable to transmit a transmit beam. A receive beamformer is operable to form a plurality receive beams in response to the transmit beam. Each of the receive beams is sampled at a plurality of depths. A processor is operable to estimate a spectrum for each of the depths of each of the receive beams and to generate display values as a function of the spectra. A display is operable to display an image of the display values.

The present invention is defined by the following claims, and nothing in this section should be taken as a limitation on those claims. Further aspects and advantages of the invention are discussed below in conjunction with the preferred embodiments.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

In a Spectral Doppler mode, multiple spatially distinct simultaneous gates are used to sample an object's motion or flow in space. For example, a beam is transmitted along a transmit angle. Using the return echoes, multiple receive beams are formed to sample the object in space at distinct ranges along and/or scan lines around the transmit beam. The transmit and corresponding receive events are repeated at regular time intervals to sample the object in time. Spectral estimation is performed at each receive range and receive scan line using a discrete Fourier transform or a Fast Fourier transform of the temporal samples. Spectra are provided for a plurality of different spatial locations and for a same period.

A display is generated as a function of the spatially distinct spectra. For example, a time-varying 1D, 2D or 3D spatial image of the Doppler frequency shift is generated as a function of the estimated spectra. Any characteristic of the spectra may be used for the spatial display, such as the maximum velocity or frequency. Velocity and frequency may be used interchangeably given the known relationship. As another example, a spectral strip is generated for a given transmit angle as a function (e.g., maximum) of the spectral estimations along multiple receive locations. The spectrum associated with the maximum velocity above an energy threshold is selected from the set of spectra and used for generating a strip display. Other characteristics of the spectra may be used for the comparison.

Spatial diversity of the spectra may be used to provide more information to the user than a spectrum for one range gate and/or color flow (mean velocity) imaging. The spectra may distinguish between types of flow, such as venous and arterial, where mean velocity may not. Velocity distribution, variation, and intensity information may be determined for multiple locations, providing more motion information.

Figure 1:
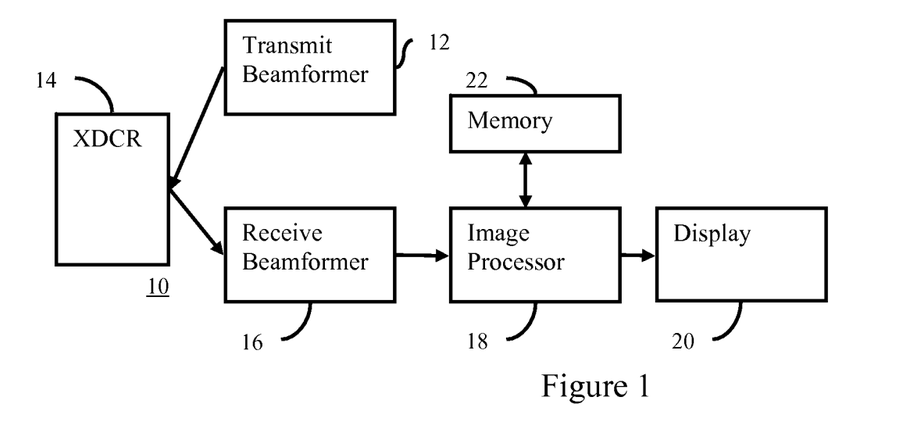
FIG. 1 is a block diagram of one embodiment of a system for displaying spatially distinct Spectral Doppler information.

FIG. 1 shows a system 10 for displaying spatially distinct Spectral Doppler information. The system 10 is a medical diagnostic ultrasound imaging system, but other imaging systems may be used, such as a workstation. The system 10 estimates spectra for different locations substantially simultaneously. Substantially accounts for sequential processing for data sampled in a same scan, such as sequential beamforming, but using the same transmit and receive event.

The system 10 includes a transmit beamformer 12, a transducer 14, a receive beamformer 16, an image processor 18, a display 20, and a memory 22. Additional, different or fewer components may be provided, such as the system 10 without the front-end beamformers 12, 16 or with a scan converter.

The transducer 14 is an array of a plurality of elements. The elements are piezoelectric or capacitive membrane elements. The array is configured as a one-dimensional array, a two-dimensional array, a 1.5D array, a 1.25D array, a 1.75D array, an annular array, a multidimensional array, combinations thereof or any other now known or later developed array. The transducer elements transduce between acoustic and electric energies. The transducer 14 connects with the transmit beamformer 12 and the receive beamformer 16 through a transmit/receive switch, but separate connections may be used in other embodiments.

The transmit beamformer 12 is shown separate from the receive beamformer 16. Alternatively, the transmit and receive beamformers 12, 16 may be provided with some or all components in common. Operating together or alone, the transmit and receive beamformers 12, 16 form beams of acoustic energy for scanning a one, two, or three-dimensional region. Vector®, sector, linear or other scan formats may be used.

The transmit beamformer 12 is a processor, delay, filter, waveform generator, memory, phase rotator, digital-to-analog converter, amplifier, combinations thereof, or any other now known or later developed transmit beamformer components. In one embodiment, the transmit beamformer 12 is the transmit beamformer disclosed in U.S. Pat. No. 5,675,554, the disclosure of which is incorporated herein by reference. The transmit beamformer 12 digitally generates envelope samples. Using filtering, delays, phase rotation, digital-to-analog conversion and amplification, the desired transmit waveform is generated. Other waveform generators may be used, such as switching pursers or waveform memories.

The transmit beamformer 12 is configured as a plurality of channels for generating electrical signals of a transmit waveform for each element of a transmit aperture on the transducer 14. The waveforms are unipolar, bipolar, stepped, sinusoidal, or other waveforms of a desired center frequency or frequency band with one, multiple, or fractional number of cycles. The waveforms have relative delay and/or phasing and amplitude for focusing the acoustic energy. The transmit beamformer 12 includes a controller for altering an aperture (e.g. the number of active elements), an apodization profile (e.g., type or center of mass) across the plurality of channels, a delay profile across the plurality of channels, a phase profile across the plurality of channels, center frequency, frequency band, waveform shape, number of cycles and combinations thereof.

The transmit beamformer 12 is operable to transmit a transmit beam of ultrasound energy. The transmit beam originates from the transducer 14 at a location in the transmit aperture. The transmit beam is formed along a scan line at any desired angle. The acoustic energy is focused at a point along the scan line, but multiple points, line focus, no focus, or other spread may be used. The transmit beam substantially covers a wide region, such as being divergent, a plane wave, collimated, unfocussed, weakly focused, or focused to cover multiple receive lines. Substantially accounts for sufficient acoustic energy to provide echoes and imaging above noise. In one embodiment, the transmit beam is sufficiently wide to cover up to 64 receive beams or scan lines distributed in a column (e.g., 8×8), a plane (1×64), or arrangements (e.g., 4×16). By controlling the apodization, aperture, and delay profile, different size regions may be scanned with a given transmit beam.

The receive beamformer 16 is a preamplifier, filter, phase rotator, delay, summer, base band filter, processor, buffers, memory, combinations thereof, or other now known or later developed receive beamformer component. Analog or digital receive beamformers capable of receiving one or more beams in response to a transmit event may be used. For example, the receive beamformer 16 has sufficient processing power and/or hardware components to substantially simultaneously form 64 or other number of receive beams in response to a same transmit. Parallel and/or sequential processing may be used to form different beams. Parallel beamforming may be provided without storing ultrasound samples for each element for an entire receive event in a memory. Alternatively, a memory may be used to store the ultrasound samples for each element.

The receive beamformer 16 is configured into a plurality of channels for receiving electrical signals representing echoes or acoustic energy impinging on the transducer 14. A channel from each of the elements of the receive aperture within the transducer 14 connects to an amplifier and/or delay for applying apodization amplification. An analog-to-digital converter digitizes the amplified echo signal. The digital radio frequency received data is demodulated to a base band frequency. Any receive delays, such as dynamic receive delays, and/or phase rotations are then applied by the amplifier and/or delay. A digital or analog summer combines data from different channels of the receive aperture to form one or a plurality of receive beams. The summer is a single summer or cascaded summer. The summer sums the relatively delayed and apodized channel information together to form a beam. In one embodiment, the beamform summer is operable to sum in-phase and quadrature channel data in a complex manner such that phase information is maintained for the formed beam. Alternatively, the beamform summer sums data amplitudes or intensities without maintaining the phase information. For parallel receive operations, different delays, apodization, and summing are provided for the different beams. Other receive beamformation may be provided, such as with demodulation to an intermediate frequency band and/or analog-to-digital conversion at a different part of the channel.

Beamforming parameters including a receive aperture (e.g., the number of elements and which elements used for receive processing), the apodization profile, a delay profile, a phase profile, imaging frequency, and combinations thereof are applied to the receive signals for receive beamforming. For example, relative delays and amplitudes or apodization focus the acoustic energy along one or more scan lines. A control processor controls the various beamforming parameters for receive beamformation.

One or more receive beams are generated in response to each transmit beam. For example, up to 64 or other number of receive beams are formed in response to one transmit beam. Acoustic echoes are received by the transducer 14 in response to the transmit beam. The echoes are converted into electrical signals by the transducer 14, and the receive beamformer 16 forms the receive beams from the electrical signals. The receive beams are collinear, parallel and offset or nonparallel with the corresponding transmit beam. The receive beams may be adjusted to account for spatial two-way differences, such as adjusting the delay profile and/or amplitude differently for receive beams closer to the transmit beam center than for receive beams spaced further from the transmit beam center. Alternatively, a single receive beam is generated for each transmit beam.

The receive beamformer 16 outputs data representing different spatial locations of a scanned region. The receive beamformer 16 generates samples at different depths along each receive beam. The ultrasound data is coherent (i.e., maintained phase information), but may include incoherent data. Once the channel data is beamformed or otherwise combined to represent spatial locations of the scanned region, the data is converted from the channel domain to the image data domain.

The image processor 18 includes a Spectral Doppler processor and/or imaging detectors. The image processor 18 is a general processor, control processor, digital signal processor, application specific integrated circuit, field programmable gate array, analog circuit, digital circuit, combinations thereof or other now known or later developed device for processing.

Figure 2:
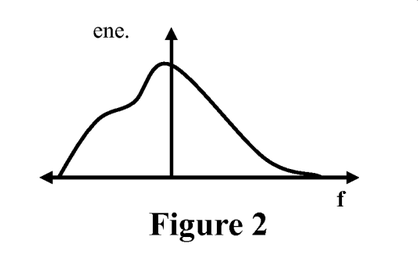
FIG. 2 is a graphical representation of a spectra.

In one embodiment, the image processor 20 is a digital signal processor or other device for applying a transform to the receive beam data. A sequence of transmit and receive events is performed over a period. A buffer or the memory 22 stores the receive beamformed data from each transmit and receive event. Any pulse repetition interval may be used for the transmit beams. Any number of transmit and receive events may be used for determining a spectrum, such as three or more. The image processor 20 is operable to estimate a spectrum for each of the depths of each of the receive beams. By applying a discrete or fast Fourier transform, or other transform to the ultrasound samples for the same spatial location, the spectrum representing response from the location is determined. A histogram or data representing the energy (ene.) level at different frequencies for the period of time to acquire the samples is obtained. FIG. 2 shows one example spectrum (ene. as a function of frequency, f) for a spatial location.

By repeating the process, the image processor 20 may obtain different spectra for a given location at different times. Overlapping data may be used, such as calculating each spectrum with a moving window of selected ultrasound samples. Alternatively, each ultrasound sample is used for a single period and spectrum.

A spectrum is determined for each of a plurality of spatial locations, such as for over 200 depths on each of 64 or other number of receive beams. The data for each location is transformed. The image processor 18 may include a plurality of components for parallel processing or a single component. The scan region may be shifted, such as transmitting and receiving at different locations. Any scan pattern may be used. For example, a volume is scanned. Transmit beams are scanned along one dimension before being shifted along another dimension to perform a planar scan (e.g., for a plurality of transmit beams at different angles in azimuth, and then repeat the different angles in azimuth but for a different elevation position). The scan pattern may provide for complete acquisition of sufficient samples for transform before shifting location or interleave the transmit beam locations with the sampling for transform.

The size of the region of interest for which spectra are acquired may be the entire image or a sub-region of the scan region. The region of interest may be increased at lower Doppler frequency or velocity scales by introducing a flow-sample-interleave mechanism similar to Color Doppler (2D or mean velocity) imaging. Tradeoffs between the number of range-gates and the lateral dimension address processing-bandwidth limitations. For example, a frequency of 2 MHz and a depth of 160 cm (i.e. the Nyquist velocity is 0.9 m/sec) is provided with a velocity scale setting of 0.45 m/sec. The number of transmit lines may be increased by a factor of 2 through an interleave factor of 2, providing a twice larger ROI size.

Data rate or processing bandwidth may be reduced for Spectral Doppler. A mean velocity image may be acquired and used to determine the location of a region of interest for acquiring spectra. Alternatively, different sparsely spaced or all regions are sampled. For example, instead of computing the Doppler spectrum at all locations and/or with full sampling, a first pass of Color Doppler estimation with thresholding over any number (e.g., 8) firings samples different the regions where Spectral Doppler estimation is to be done and also determines if multiple firings (64 or 128) are appropriate for that scan angle. This may improve the frame-rate and increase the ROI size in azimuth and elevation by avoiding some firing angles, and avoid processing for tissue regions.

Automatic velocity scale identification for Color Doppler imaging may be provided. The spectral velocity estimates on a few sparse spectral firings are acquired. The mean velocity or the maximum velocity are determined from the spectra or a spectrum. The velocity scale is set for Color Doppler accordingly.

The image processor 18 generates display values as a function of the spectra. Display values include intensity or other values to be converted for display, values provided to the display 20 (e.g., red, green, blue values), or analog values generated to operate the display 20. The display values may indicate intensity, hue, color, brightness, or other pixel characteristic. For example, the color is assigned as a function of one characteristic of a spectrum and the brightness is a function of another spectrum characteristic or other information. The display values may be combined with other display values, such as blending or overlaying display values determined, at least in part, from spectral information with B-mode information.

The display values are generated as a function of the spatial spectral information in any type of display format. For example, the display values are generated for a spectral strip display. The different spectra are compared. The spectrum with the highest velocity over a noise floor is selected for display. A spectrum for a location with an averaged maximum velocity over time may be selected. The selected spectrum is used for the spectral display. The spectra for the same location are used over time. Alternatively, the spectrum with the highest velocity is used for each time increment of the spectral strip regardless of location.

In another embodiment, a one, two, or three-dimensional representation is generated. For example, display values are generated for a two-dimensional image representing a region sampled by the receive beams. A display value is provided for each pixel and/or sample location. The display values for each location of the two-dimensional image are a function of the respective spectrum. For example, the maximum velocity is identified in each spectrum. The display values are modulated by the maximum velocities, such as mapping color and/or brightness based on the maximum velocity. Any mapping may be used, such as color mapping used for color flow.

The image processor 18 may include a B-mode detector for determining intensity and/or a Doppler detector for determining average velocity, variance, and/or energy. One or more filters, such as clutter, spatial or temporal filters may be provided. The detector outputs incoherent image data. Additional processes, such as filtering, interpolation, and/or scan conversion, may be provided by the image processor 18.

A spatial image may be generated as a function of both spectra and mean velocity. The difference between Color Doppler (qualitative) and Spectral Doppler (quantitative) methods is blurred or blended. The number of firings at a given scan-angle is increased to get the spectrum (quantitative). The number of firings to get Color Doppler (qualitative) is decreased. A sparse-sampled Spectral Doppler firing scheme is combined with a finer-sampled Color Doppler acquisition scheme (e.g. assume 16 firing angles where 4 are used for Spectral Doppler estimation and the rest are used for Color Doppler estimation). A quantitative Color Doppler image is provided by combining the spectral velocity information and the color-doppler velocity information with interpolation. A moving average of the color-samples indicates quantitative Color Doppler.

The display 18 is a CRT, monitor, LCD, plasma screen, projector or other now known or later developed display for displaying an image responsive to the display value. For a black and white Spectral Doppler image, a range of velocities with each velocity modulated as a function of energy is provided as a function of time. The selected spectrum indicates the velocity and energy information for a given time. The intensity of a given pixel or pixel region represents energy where velocity is provided on the vertical scale and time provided on the horizontal scale. Other image configurations may be provided, including colorized Spectral Doppler images. For spatial imaging, an M-mode type image of maximum velocity or other characteristic determined from the spectra along a line is provided. The brightness along a line is mapped as a function of time. A two-dimensional image may be generated from the display values. Display data representing a volume may be rendered using any three-dimensional imaging.

The memory 22 stores buffered data, such as ultrasound samples for spectrum estimation. The memory 22 may store display values or images, such as a CINE memory. In one embodiment, the memory 22 is a computer readable storage medium having stored therein data representing instructions executable by the programmed processor 18 for displaying spatially distinct Spectral Doppler information. The instructions for implementing the processes, methods and/or techniques discussed herein are provided on computer-readable storage media or memories, such as a cache, buffer, RAM, removable media, hard drive or other computer readable storage media. Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

Figure 3:
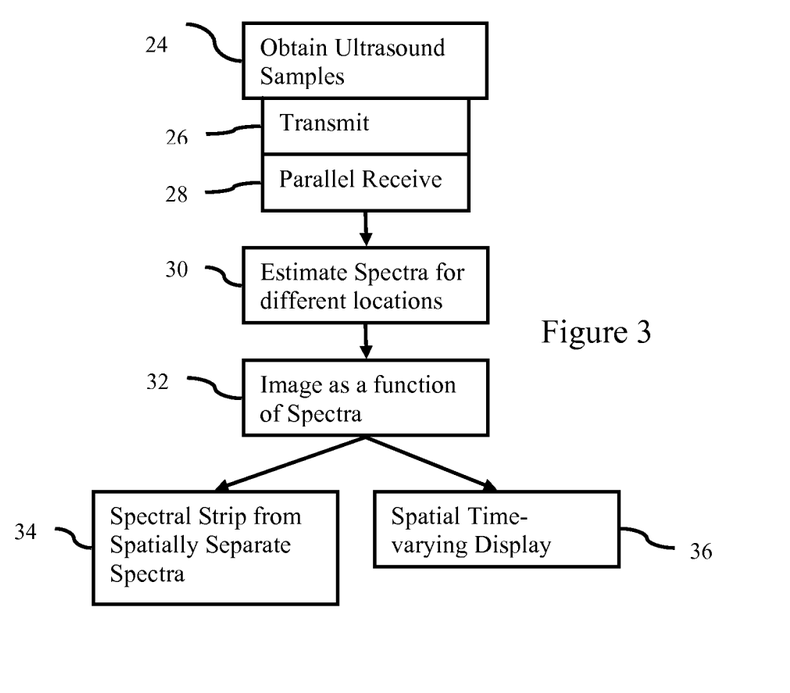
FIG. 3 is a flow chart diagram of one embodiment of a method for displaying spatially distinct Spectral Doppler information.

FIG. 3 shows method for displaying spatially distinct Spectral Doppler information. The method is implemented on the system 10 of FIG. 1 or a different system. The acts are performed in the order shown, but other orders are possible. Additional, different, or fewer acts may be provided, such as obtaining the samples in act 24 without the transmission and reception of acts 26 and 28. Acts 34 and 26 are alternatives, may be performed together, or are not provided.

In act 24, ultrasound samples are obtained for a plurality of spatially distinct locations. The sampled are obtained by transfer from memory or by scanning in real-time. For example, a transmission is performed in act 26. A plurality of scan lines and ranges along the scan lines are sampled in act 28 in response to the single transmission. Parallel receive beamforming is provided. The ultrasound samples are obtained at a substantially same time in response to a plurality of receive beams responsive to a same transmit beam. In alternative embodiments, sequential receive beamforming or a combination of parallel and sequential receive beamforming is used. Other plane wave transmission and reception techniques may be used, such as applying a Fourier transform to electrical signals at each element to generate an array of values representing response at different locations.

Ultrasound samples are obtained over a period, such as acquiring five or more ultrasound samples for each spatial location. Any scan sequence and/or pulse repetition frequency may be used.

In act 30, a spectrum is estimated for each of the spatially distinct locations. The spectra are estimated from the ultrasound samples and correspond to a period in which the samples were acquired. Different spectra may be estimated for the same spatial location at different times corresponding to different periods of acquisition. For each spatial location of interest, such as all the locations in a region of interest, in an image field, or other distributions, a spectrum is calculated. Spectra may be determined for only a subset of the spatial locations, such as determining the spectra for sparsely sampled locations or densely sampled locations but in a limited region.

A set of spectra for a given time or representing the sampling period are estimated. For parallel receive beamforming, the spectra may represent the same period. In one embodiment, all of the spatial locations for determining spectra are sampled at a same time (e.g., same transmit and receive events). In other embodiments, sequential acquisition is used. The spectra are sampled at a same time relative to a physiological cycle, such as the heart cycle. Spectra for only one period may be estimated. Alternatively, spectra for the same locations are estimated for different periods to provide time varying spectral information.

Figure 4:
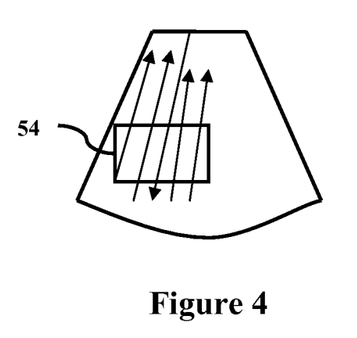
FIG. 4 is a graphical representation of parallel beamforming in a region of interest.

FIG. 4 shows one embodiment where one transmission in act 26 is used to acquire a plurality of receive beams in act 28. While four receive beams are shown, a greater density may be provided, such as eight, sixteen, thirty two, sixty-four, or other number of receive beams per transmit beam. The transmit and receive beams intersect a region of interest 54. The region of interest 54 may be larger, smaller, have a different shape, or be the entire imaging region. The region of interest 54 defines the spatial locations for which spectra are estimated. For example, at least one hundred spectra for respective spatially different spatial locations within the region of interest 54 are calculated.

The spectra are estimated by applying a Fourier transform to the ultrasound samples representing each of the spatially distinct locations. Spatially distinct locations correspond to different range gates, such as different centers positions, sizes or both, with or without overlap. Any transform may be applied to determine the spectrum for each of the spatially distinct locations. The spectra represent energy as a function of frequency (See FIG. 2).

In act 32, an image is displayed. The image is a function of the spectra for the plurality of spatially distinct locations. The spectra are used to provide information to the user in a representation of a region, as a numerical quantity, or through graphics displayed as the image. Any function may be used, such as mapping, modulating, selecting, or comparing. The image may provide information associated with only one spectrum, but be a function of spectra from different spatial locations. For example, the spectra are compared to select one of the spectra for display.

By providing spectra from different spatial locations, more information may be provided to a user than by using Color Doppler (mean) velocity, variance, or energy imaging or than by using Spectral Doppler for a given range gate. Any characteristic of the spectra may be used, such as the maximum velocity, minimum velocity, mean velocity, median velocity, energy and velocity information, maximum energy, velocity associated with maximum energy, variance of velocity, slope or trend in the spectra, or location of change of slope. Instead of the mean velocity or energy of the mean velocity, other information may be provided. Different types of spectral information may be useful for different diagnostic purposes. For example, the maximum velocity may more accurately indicate tissue health. The variance of the spectra may indicate flow conditions. The useful information provided in spectral strips is available for many locations at a same time, providing spatial distribution information. Locating the spectrum with the maximum velocity may provide better flow information than a user guessed position.

Any now known or later developed techniques may be used to characterize or determine a characteristic of the spectra. For example, the highest velocities above a threshold level with only one or no lower velocities below the threshold indicate the maximum velocity. The maximum velocity is the highest or an average of the two or more highest velocities associated with contiguous values above the threshold or noise level.

Any technique may be used to provide the spatial information to the user. In act 34, a spectral strip is used. Multiple strips may be used, where each strip represents the spectrum for a different spatial location. Only one strip may be used, but still be a function of spectra from different spatial locations. For example, one of the spectra is identified as a function of a spectral characteristic. The value of the same characteristic of the spectra is compared. One is selected, such as identifying the spectrum having a maximum frequency. The average of the characteristic over time may be used for the selection. The selection may be constant after identification. Alternatively, the selection varies as a function of time. The selection through comparison is performed periodically, every time increment of the spectral strip display, or in response to a triggering event. In other embodiments, spectra from different spatial locations are combined, such as averaging the frequency bins of a plurality of spectra from different spatial locations.

Figure 6:
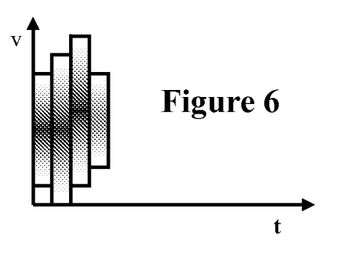
FIG. 6 is a graphical representation of a spectral strip display derived from spectra at different locations.

A spectral strip representing the selected spectrum or otherwise combined spectra is displayed. FIG. 6 shows an example spectral strip display simplified for illustration. The spectral strip shows the frequency modulated by energy as a function of time. Any now known or later developed spectral strip mapping may be used, such as gray scale mapping with the intensity representing energy. Filtering may be applied to smooth the spectrum. Characteristics of the spectral strip may be determined and displayed, such as graphically tracking a maximum velocity as a function of time in the spectral strip.

In another embodiment, a representation of a difference between spectra at different locations is displayed. The difference in flow between two spatially (or temporally) distinct acquisitions may quantitatively show flow changes over distance or time. The difference may be shown by color coding the spectra differently and overlaying or compounding them. Alternatively, a difference in amplitude at each frequency is calculated and displayed. Any difference may be used. Spectral data from a previous examination may be acquired and compared with a current spectra. The difference may be displayed to show changes over time, such as sixth months.

In one embodiment, the spectral strip is displayed with a spatial image, such as a one-dimensional M-mode, two-dimensional B-mode, two-dimensional color flow mode, or combination thereof image. The location of the selected spectrum or spectra may be indicated graphically in the image. For example, text, color, symbol, or other indicator shows the user the location for the range gate corresponding to the selected spectrum. The user may add other range gate spectral displays for comparison. Where multiple spectra are displayed, matched color coding between the acquisition range gates and displayed spectra may be used. For example, the indication of the location of the range gate uses orange. The corresponding spectrum is shaded in orange, outlined in orange, or otherwise labeled in orange. Other indications may be used, such as text labels or numbering.

In act 36, a spatial image is generated. The image is a one, two, or three-dimensional representation. A one, two, or three-dimensional region representing the spatially distinct locations is displayed. For example, an M-mode image is generated. The image represents information from spatial locations along a line or curve, shown as a function of time. As another example, a two-dimensional image of a plane is provided. In another example, a three-dimensional representation is rendered from data representing a volume.

The represented region is along a scan axis, such as azimuth, elevation, and/or range, or is along different axes. For example, an arbitrary plane is defined through a volume. Spectra from spatial locations on or near the arbitrary plane are used for generating the spatial image. In other embodiments, the plane or line is positioned along a scan axis, such as along the axis along which the scan progresses most rapidly or without interleaving to scan along another axis.

A display value for each of the spatial locations in the image is a function of a respective spectrum. The pixels may be modulated or mapped as a function of a characteristic of each spectrum, representing spectral information at each distinct spatial location. For example, the maximum velocity is determined for each spatial location within a region of interest. Full or sparse sampling may be used. Other Doppler frequency shift or spectral characteristics may be used. Since different spectra may result at different locations due to different tissue movement or flow, the spatial image displays the variance in spectra as a function of space. Due to filtering or combining of spectra, the spectrum for a distinct spatial location may be a function of multiple spectra.

In one embodiment, the spectra are used to classify a type of flow or motion, and the mapping function or other display value characteristic is selected based on the classification. For example, the spectra may distinguish between arterial and venous flow for each of the spatially distinct locations. Arterial flow may have greater velocity or frequency variation, higher maximum velocity, or other characteristics at a given time for arterial flow. The variance as a function of time may distinguish an arterial flow location from a venous flow location.

Any characteristic of the image may vary as a function of the spectral information. For example, the grey scale level, the color, the hue, the brightness, or other characteristic varies with variation in the spectra characteristic. In the arterial verses venous flow example above, arterial and venous flow may be represented by different colors, such as B-mode, mean velocity, or other values assigned a base color of red or blue depending on being an arterial or venous flow location (i.e., similar to color flow mapping for velocity to and away from the transducer). The brightness or shade of each color is a function of different information, such as the maximum or mean velocity. As another example, the display value is modulated or varies as a function of the maximum velocity derived from each spectrum. The other characteristics of a given pixel may be a function of information from the spectra or different information.

The image may be displayed as a function of time. The one, two, or three-dimensional image varies as a function of time. The image is re-generated with more recently acquired spectral or other information. For example, a moving window defines the most recently acquired data set, such as the most recent 5-10 samples with the window shifting by 1, 2, or other number of samples, for calculating the spectra. The most recent spectral information is used to generate the image of the region. The image changes as the spectra and/or other information change.

Further processing may be provided, such as spatial or temporal filtering. The filtering may be applied to the spectra, data used to determine the spectra, the display values, or other information.

Figure 5:
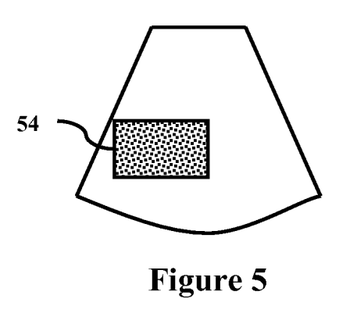
FIG. 5 is a graphical representation of a two-dimensional display of information derived from spectra at different locations.

The image or images based, at least in part, on spectral information are displayed alone. The image or images may overlay other information, such as being a combination of spectral information and B-mode information. FIG. 5 shows a B-mode scan region with B-mode information in grey scale. The spectral information is displayed in a region of interest 54 in color. The pixels for the region of interest are not responsive to the B-mode information. Alternatively, the B-mode information also modulates the pixels in the region of interest 54, such as displaying the color spectral information as a semi-transparent overlay of the B-mode gray scale information.

Other images may be displayed. For example, a B-mode image, color flow image, or combined B-mode and color flow image is displayed adjacent to but separate from a spectral strip image or other image based, at least in part, on spectral information from different spatial locations. Separate images on a same display at a same time may be used with or without overlap.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

We claim:

1. A method for displaying spatially distinct Spectral Doppler information, the method comprising:
   obtaining, with an ultrasound imaging system, spatial and temporal ultrasound samples for a plurality of spatially distinct locations in a patient, the obtaining being simultaneously for gates at the plurality of spatially distinct locations;
   estimating, by spectral Doppler processor, a spectrum for each of the spatially distinct locations from the temporal ultrasound samples, the spectrum at each of the spatially distinct locations comprising energy as a function of frequency for the respective location; and
   generating and displaying a image on a display, the image being a two or three dimensional representation and being a function of the spectra for the plurality of spatially distinct locations with different pixels of the image representing the respective distinct locations, wherein the displaying the image comprises representing the spatially distinct locations distributed in two or three-dimensions and the image not being spectral strips of the spectra, a display value for each pixel of the respective spatially distinct locations being a function of the respective spectrum.

2. The method of claim 1 wherein the obtaining comprises obtaining the spatial ultrasound samples at a substantially same time in response to a plurality of receive beams responsive to a same transmit beam.

3. The method of claim 1 wherein the obtaining comprises sampling along a plurality of scan lines and ranges.

4. The method of claim 1 wherein the obtaining comprises obtaining a plurality of the spatial ultrasound samples for each of the plurality of spatially distinct locations, and wherein the estimating comprises applying a Fourier transform to the temporal ultrasound samples representing each of the spatially distinct locations.

5. The method of claim 1 further comprising:
   identifying a first of the spectra as a function of a spectral characteristic; and
   displaying a spectral strip representing the first of the spectra.

6. The method of claim 5 wherein the identifying the first of the spectra comprises identifying the first of the spectra having a maximum frequency.

7. The method of claim 1 wherein the display value for each pixel of the spatially distinct locations is a function of a maximum velocity of the respective spectrum.

8. The method of claim 1 further comprising distinguishing between arterial and venous flow for each of the spatially distinct locations as a function of the respective spectrum, and wherein the display value for each of the spatially distinct locations is a function of the distinction between arterial and venous flow.

9. The method of claim 1 further comprising color coding a spatially distinct location associated with a first of the spectra in a corresponding manner.

10. The method of claim 1 further comprising:
    adapting a region of interest as a function of estimated spectra including the spectrum, the region of interest being for estimating additional spectra.

11. The method of claim 1 further comprising:
    determining a velocity scale as a function of the spectrum at each of the spatially distinct locations.

12. In a non-transitory computer readable storage medium having stored therein data representing instructions executable by a programmed spectral processor for displaying spatially distinct Spectral Doppler information, the storage medium comprising instructions for:

calculating, with a spectral processor, a first spectrum for a first spatial location and a first period of time, the first spectrum comprising energy distribution over frequency for the first spatial location;

calculating, with the spectral processor, a second spectrum for a second spatial location and the first period of time, the second spatial location along a different line than the first spatial location, the second spectrum comprising energy distribution over frequency for the second spatial location; and generating, on a display, a sequence of images including a first image that is a function of the first and second spectra and is a function of additional spectra from repetition of the calculations for additional spatially different spatial locations across a two or three-dimensional region for the first period of time, the images of the sequence other than the first image being from repetition of the calculations for other periods of time, wherein the generating the sequence of images comprises displaying a time varying two or three-dimensional spatially distributed representation of a Doppler frequency shift, the Doppler frequency shift in the first image at the first, second and additional spatial locations determined as a function of the first, second and additional spectra, respectively, for the first period of time, the time varying representation being the sequence of images displayed over the other periods of time, each pixel of a respective image in the sequence of images at a given period of time representing a different one of the spatial locations and corresponding Doppler frequency shift determined as a function of the spectra of the repetition of the calculations for the respective given period of time.

13. The non-transitory computer readable storage medium of claim 12 wherein the calculating of the first and second spectra comprises of applying a Fourier transform to ultrasound samples acquired during the first period from first and second scan lines, respectively, in response to a same transmit event, the first spatial location on the first scan line and the second spatial location on the second scan line.

14. The non-transitory computer readable storage medium of claim 12 further comprising instructions for calculating at least one hundred additional spectra for the respective spatially different spatial locations, and wherein generating the sequence of images comprises generating each image of the sequence as a function of the respective first, second and additional spectra.

15. A system for displaying spatially distinct Spectral Doppler information, the system comprising:

a transmit beamformer configured to transmit a transmit beam;

a receive beamformer configured to form a plurality of spatially distinct receive beams sampling a two or three dimensional region in response to the transmit beam;

a processor configured to estimate a spectrum for each of the depths of each of the receive beams, each spectrum comprising energies as a function of frequency, and to generate display values as a function of the spectra, the display values representing information derived from the spectra and being for pixels distributed in two dimensions representing a two or three dimensional distribution of sample locations of the spectra; and a display configured to display an image of the display values.

16. The system of claim 15 wherein the processor is operable to generate the display values for the image representing the region sampled by the receive beams, the display values for each location of the image being a function of the respective spectrum.

17. The system of claim 16 wherein the display values are a function of maximum velocities from the spectra.

18. The system of claim 15 wherein the processor is operable to generate the display values for the region sampled by the receive beams, the display values for each location of the image being a function of the respective spectrum.

19. The system of claim 15 wherein each of the receive beams are sampled at a plurality of depths.

* * * * *